United States Patent
Rafiee (10) Patent No.: US 7,442,207 B2
(45) Date of Patent: Oct. 28, 2008

(54) DEVICE, SYSTEM, AND METHOD FOR TREATING CARDIAC VALVE REGURGITATION

(75) Inventor: Nasser Rafiee, Andover, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 170 days.

(21) Appl. No.: 11/409,249

(22) Filed: Apr. 21, 2006

(65) Prior Publication Data

US 2007/0250160 A1    Oct. 25, 2007

(51) Int. Cl.
A61F 2/24    (2006.01)
(52) U.S. Cl. ..................................... 623/2.37
(58) Field of Classification Search ............... 623/2.37, 623/2.11–2.36, 2.38–2.42; 606/198
See application file for complete search history.

(56) References Cited

U.S. PATENT DOCUMENTS

| | | | |
|---|---|---|---|
| 4,887,601 A | | 12/1989 | Richard |
| 5,246,443 A | | 9/1993 | Mai |
| 5,342,396 A | | 8/1994 | Cook |
| 5,690,670 A | * | 11/1997 | Davidson .................... 606/198 |
| 5,728,068 A | | 3/1998 | Leone et al. |
| 6,231,561 B1 | * | 5/2001 | Frazier et al. ............... 604/500 |
| 6,348,064 B1 | * | 2/2002 | Kanner ....................... 606/219 |
| 6,565,603 B2 | | 5/2003 | Cox |
| 6,932,838 B2 | | 8/2005 | Schwartz et al. |
| 7,288,097 B2 | * | 10/2007 | Seguin ....................... 606/142 |
| 2002/0002401 A1 | | 1/2002 | McGuckin et al. |
| 2004/0260394 A1 | | 12/2004 | Douk et al. |
| 2006/0241748 A1 | * | 10/2006 | Lee et al. .................... 623/2.37 |
| 2007/0093869 A1 | * | 4/2007 | Bloom et al. ............... 606/219 |

FOREIGN PATENT DOCUMENTS

| | | |
|---|---|---|
| WO | WO02/094132 | 11/2002 |
| WO | WO 2004112652 A2 * | 12/2004 |

* cited by examiner

*Primary Examiner*—William H. Matthews
*Assistant Examiner*—Ann Schillinger (57) ABSTRACT

A device, a system and a method for treating heart valve regurgitation. The annulus reshaping device comprises a base and a plurality of legs radially arranged there upon. The device can transform from a delivery configuration wherein it is deliverable by catheter to a treatment site, into a deployment configuration, and then a treatment configuration for treating valvular regurgitation. The device is implanted into the annulus of a heart valve, and the legs of the device can be telescopically withdrawn to apply an inward force to the annulus. The system comprises a device slidably received within a catheter. The method of treatment comprises delivering a device to a treatment area, via catheter, releasing the device from the catheter, positioning the legs of the device on a valve annulus, and applying an inward force to the annulus to reduce the regurgitation.

9 Claims, 11 Drawing Sheets

DEVICE, SYSTEM, AND METHOD FOR TREATING CARDIAC VALVE REGURGITATION

TECHNICAL FIELD

This invention relates generally to medical devices and particularly to a device, system, and method for altering the shape of a heart valve annulus.

BACKGROUND OF THE INVENTION

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the bicuspid mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets overlap during contraction of the left ventricle and prevent blood from flowing back into the left atrium. However, due to various cardiac diseases, the mitral valve annulus may become distended, causing the leaflets to remain partially open during ventricular contraction and thus allowing regurgitation of blood into the left atrium. This results in reduced ejection volume from the left ventricle, causing the left ventricle to compensate with a larger stroke volume. The increased workload eventually results in dilation and hypertrophy of the left ventricle, further enlarging and distorting the shape of the mitral valve. If left untreated, the condition may result in cardiac insufficiency, ventricular failure, and death.

It is common medical practice to treat mitral valve regurgitation by valve replacement or repair. Valve replacement involves an open-heart surgical procedure in which the patient's mitral valve is removed and replaced with an artificial valve. This is a complex, invasive surgical procedure with the potential for many complications and a long recovery period.

Mitral valve repair includes a variety of procedures to reshape or reposition the leaflets to improve closure of the valve during ventricular contraction. Correction of the regurgitation may not require repair of the valve leaflets themselves, but simply a reduction in the size of the mitral valve annulus, which can become distended. A common repair procedure involves implanting an annuloplasty ring on the mitral valve annulus. The annuloplasty ring generally has a smaller diameter than the distended annulus, and when sutured to the annulus, the annuloplasty ring draws the annulus into a smaller configuration, bringing the mitral valve leaflets closer together and providing improved closure during ventricular contraction.

Annuloplasty rings may be rigid, flexible, or have both rigid and flexible segments. Rigid annuloplasty rings have the disadvantage of causing the mitral valve annulus to be rigid and unable to flex in response to the contractions of the ventricle, thus inhibiting the normal movement of the mitral valve that is required for it to function optimally. Flexible annuloplasty rings are frequently made of Dacron® fabric and must be sewn to the annular ring with a line of sutures. Scar tissue formation from the multiple stitches may lead to loss of flexibility and function of the mitral valve. Similarly, combination rings must generally be sutured in place and also cause scar tissue formation and loss of mitral valve flexibility and function.

Annuloplasty rings have been developed that do not require suturing. U.S. Pat. No. 6,565,603 discloses a combination rigid and flexible annuloplasty ring that is inserted into the fat pad of the atrioventricular groove, which surrounds the mitral valve annulus. Although this device avoids the need for sutures, it must be placed within the atrioventricular groove with great care to prevent tissue damage to the heart.

Therefore, it would be desirable to provide a device, system, and method for treating mitral valve regurgitation that overcome the aforementioned and other disadvantages.

SUMMARY OF THE INVENTION

One aspect of the present invention is a device for altering the shape of a heart valve annulus, comprising a base and a plurality of legs radially extending from the base. Each leg includes a tip for piercing engagement with the valve annulus. A rotational force will transform the device from a deployed state to a treatment state. The treatment state will apply a reshaping force to the valve annulus engaged by the tips. Each leg may comprise an inner section and an outer section that are slidably connected wherein the tip of the outer member will retract toward the base in response to application of the sufficient force on an adjustment cord.

Another aspect of the present invention is a system for altering the shape of a heart valve annulus that includes the above-described annulus reshaping device and further comprises a delivery catheter. The annulus reshaping device is elastically collapsible to be slidably received within a lumen of the delivery catheter.

Yet another aspect of the present invention is a method of altering the shape of a heart valve annulus. An annulus reshaping device is delivered in a lumen of a catheter proximate a treatment area. The annulus reshaping device is released from the catheter. Legs of the annulus reshaping device are positioned on valve annulus to be contracted and the device is secured to the annulus. The legs of the device are then altered so that the distance between a base of the device and tips of the legs is less than it was when the device was initially secured to the annulus. The shape of the valve annulus is altered in response to the shortening of the legs, and the leaflets of the valve may achieve greater coaption as a result.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

DETAILED DESCRIPTION

The invention will be describe by reference to the drawing figures, where like numbers refer to like parts. The current invention discloses therapeutic devices and methods for treating valvular regurgitation by altering the shape of a cardiac valve, which in turn increases coaption of the valve leaflets. These therapeutic devices will be described below and will be referred to herein using the terms "device" or "devices." Although described below in the context of treating mitral valve regurgitation by radially contracting portions of the valve annulus, the devices of the invention may also be deployed at other locations in the body.

The devices disclosed and discussed herein may be made from a suitable biocompatible material including a suitable biocompatible shape-memory material or a suitable biocompatible super elastic material. Embodiments of the devices disclosed herein may be made from biocompatible plastics, biocompatible metals, biocompatible alloys, or a combination thereof. Examples of biocompatible plastics include, but are not limited to, polyurethane, polyethylene, polyamide, fluoropolymers such as fluorinated ethylene propylene (FEP) or polytetrafluoroethylene (PTFE), polyether-block amide (PEBA) co-polymer, or co-polymers thereof. Examples of biocompatible metals and metal alloys include, but are not limited to a nickel-titanium alloy, a nickel-cobalt alloy, another cobalt alloy, stainless steel, combinations thereof, and the like. In at least one embodiment, the entire device may be composed of a shape memory metal alloy that will achieve the desired mechanical profile (the treatment state) when the device is released from the delivery catheter.

An antithrombotic component may be included in the chemical composition of a polymer used to form the device. Optionally, a polymeric or metallic device may be coated with a polymer that releases an anticoagulant and thereby reduces the risk of thrombus formation. If desired, additional therapeutic agents or combinations of agents may be used, including antibiotics and anti-inflammatories.

The devices of the current invention may also be made, in whole or in part, from one or more materials that are viewable by radiography, ultrasound, or magnetic resonance imaging, visualization techniques. Embodiments of the devices may also be coated with materials that are visible using such visualization methods. Some embodiments of the devices comprise a combination of materials that allows for viewing an image of the device using two or more of the above-mentioned techniques.

Some embodiments of the devices can include materials having a high X-ray attenuation coefficient (radiopaque materials). The devices may be made in whole or in part from the material, or they may be coated in whole or in part by radiopaque materials. Alloys or plastics may include radiopaque components that are integral to the materials. Examples of suitable radiopaque material include, but are not limited to gold, tungsten, silver, iridium, platinum, barium sulfate and bismuth sub-carbonate.

When used to discuss the deployment of the devices disclosed herein, the terms "distal" and "proximal" are used with reference to the treating clinician. When used to discuss the devices disclosed herein, the terms are used with reference to the base of the device. "Distal" indicates an apparatus portion distant from, or a direction away from the clinician or base and "proximal" indicates an apparatus portion near to, or a direction towards the clinician or base.

Figure 1:
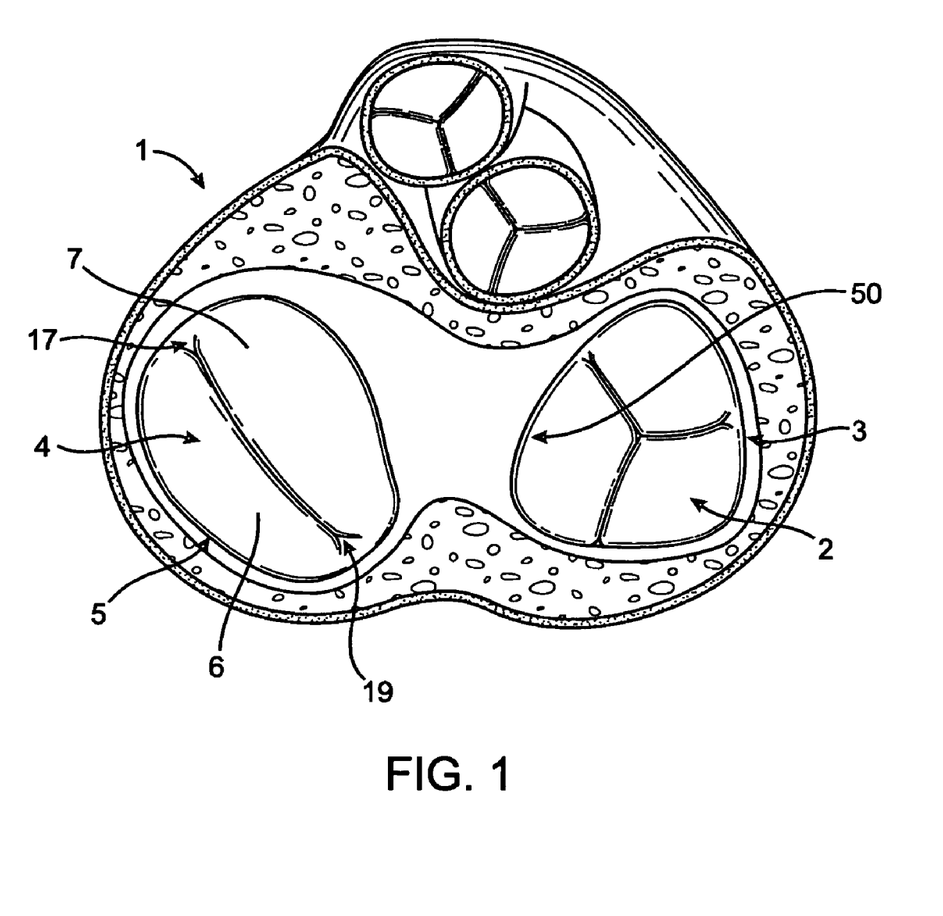
FIG. 1 is cross sectional schematic view of a heart showing the location of the heart valves.

One aspect of the present invention is a device for altering the shape of a heart valve annulus. Referring to the drawings, FIG. 1 shows a cross-sectional view of heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. Also shown in the figure are the posterior commisure 19 and the anterior commisure 17.

The devices of the current invention can be delivered to, and implanted in, a beating heart using minimally invasive surgical techniques or via catheter based delivery through the vascular system. The devices may also be implanted during more traditional open heart surgery on a heart that has been temporarily halted. Where devices are delivered using minimally invasive surgical procedures, the delivery instruments can be inserted through the wall of the atrium at a location directly adjacent to the posterior commisure, or a location on the approximate top center of the atrium. If the devices are delivered to the atrium via catheter, the catheter can enter the atrium through an opening created in the septal wall between the left and right atrium. In one embodiment, the opening is created in the area of the fossa ovalis 50.

Figure 2:
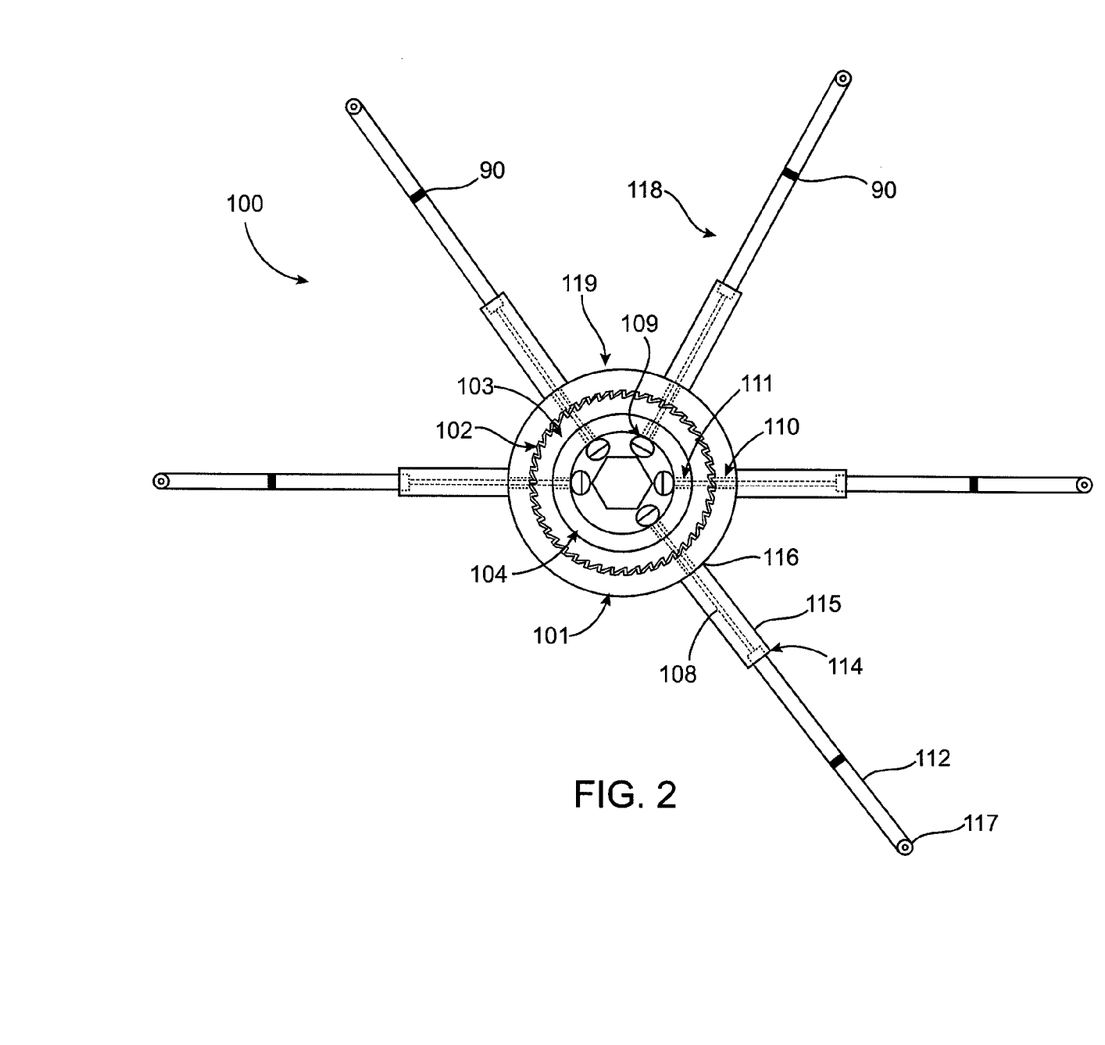
FIG. 2 is a plan view of a device for treating heart valve regurgitation, according to the current invention.

Referring now to FIG. 2 a preferred embodiment of the current invention comprises a base/hub 119 having a generally circular exterior perimeter, and a plurality of tissue engaging, telescopic legs 118 extending from the base. Starting from the distal most tip, each leg has a tissue engaging tip 117, an outer leg member 112, and an inner leg member 115. The inner leg members 115 can be attached to the outer ring 101 of the base, or the base and inner leg members can be made from the same piece of material such that the inner leg members are integral to the outer ring. An adjustment ring 104 is inside of the outer ring. An adjustment cord extends from the proximal end of each outer leg member to the adjustment ring. Each leg may include one or more radiopaque markers 90 to assist a clinician in visualization/imaging during while implanting the device.

Figure 5:
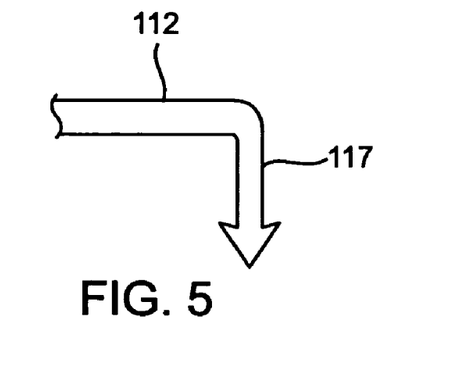
FIG. 5 is an illustration of the tissue engaging portion of the device of FIG. 2
Figure 6:
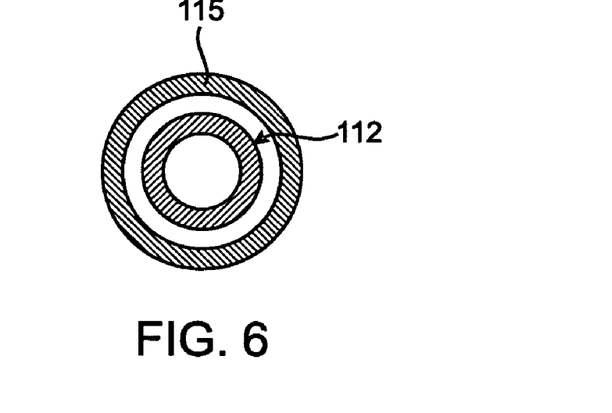
FIGS. 6 and 7 are cross-sectional views of embodiments for the configuration of telescopic legs of the devices of the current invention.
Figure 7:
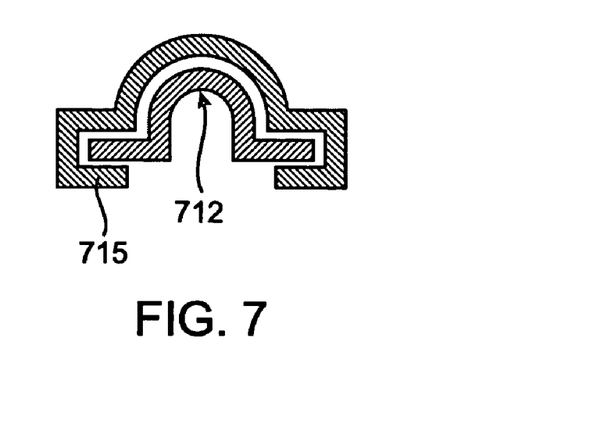

Referring now to FIGS. 5-7 the legs of the devices are made such that the outer leg member 112 and inner leg member 115 are arranged in a telescoping relationship. In preferred embodiments of the invention, the two leg members have complementary shapes and the outer leg member is disposed inside of the inner leg member.

In the embodiment of the invention depicted in FIG. 6, the outer leg member and the inner leg members have circular or round transverse cross-sections. The inner leg member is a tubular member 115 is an elongated tubular member and the outer leg member 112 can be an elongated tubular member, or it can be a solid elongated member. The inner leg member has a slight lip on the interior surface of the member, and the outer leg member has a flange on the exterior of the proximal end of the member (at 114 of FIG. 2) to prevent the outer member from extending out of the inner leg member. FIG. 7 shows another embodiment of the current invention having leg members with a generally omega-shaped (Ω) transverse cross section.

Regardless of the cross sectional shape of the leg members, an annulus engaging tip is located at the distal end of each outer leg member. Referring to FIG. 5, one embodiment of the invention has annulus engaging tips 117 that are integral to the outer leg member 112, and the tips 117 are barbed so that they can be securely implanted into a valve annulus. The tips on the depicted embodiment are formed such that they will point down toward a valve annulus when the device is deployed in a heart. Other shapes and embodiments of tips are possible, including tips similar to the snap acting tips of the devices depicted in the U.S. Patent application having the Ser. No. 60/480,364, titled "METHOD AND SYSTEM FOR REDUCING MITRAL VALVE REGURGITATION," filed on Dec. 15, 2005 by Nareak Douk et al., the entire contents of which are incorporated herein by reference thereto.

As noted above, the inner leg members 115 can be attached to the base member or they can be made from the same piece of material as the outer ring 101. In one embodiment, the inner leg members are spot welded to the outer ring. In another preferred embodiment, the inner leg members have a threaded portion that is engaged with complementary threads in the adjustment cord channels 110 in the outer ring. The inner leg members are made from a biocompatible material having sufficient elasticity to allow the device to be built in a deployment configuration, bent into a delivery configuration so that the device can be delivered to a heart valve via catheter, and then change back to the deployment configuration when the device is deployed from the catheter. Examples of such materials are noted above, in one preferred embodiment the inner leg members and outer ring are made from a cobalt based alloy and in another embodiment the inner leg members and outer ring are made from nitinol. The outer leg members and the tips of the devices can be made from any suitable biocompatible material. In one embodiment the outer leg members are made from a cobalt alloy, in another embodiment the outer leg members are made from nitinol and in another embodiment the outer leg members are made from the same material that the inner leg members and the outer ring are made from.

Figure 3:
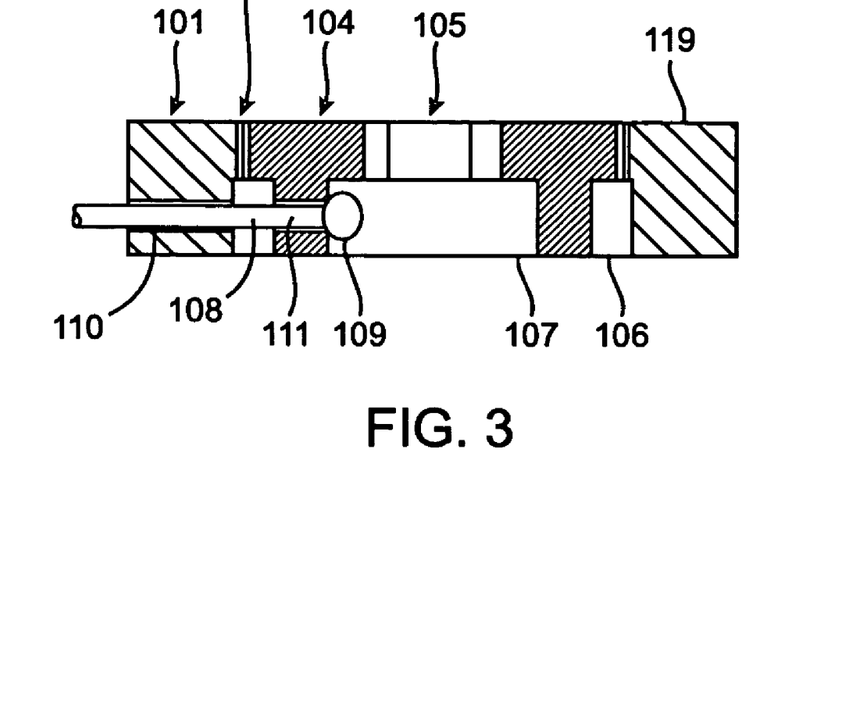
FIG. 3 is a longitudinal cross sectional view showing the components of the device of FIG. 2 in greater detail.
Figure 4:
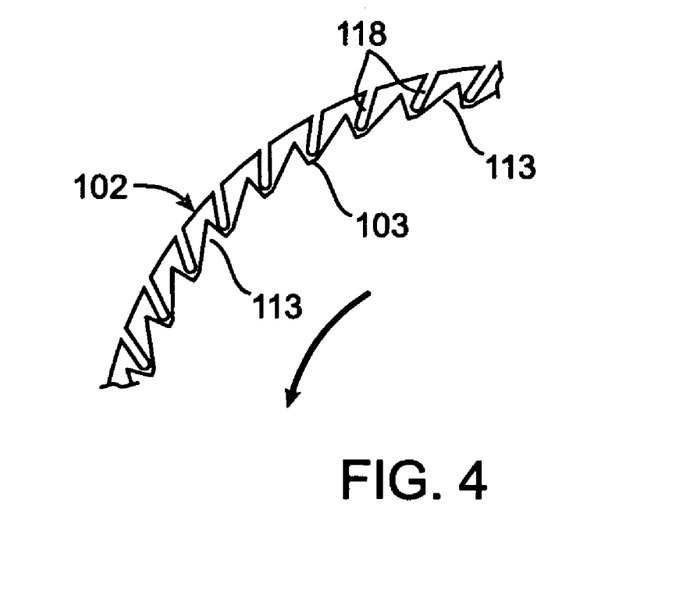
FIG. 4 is an exploded view showing the locking mechanism of the device of FIG. 2 in greater detail.

Referring now to FIGS. 2-4, the base of the device comprises an outer ring 101 and an adjustment ring 104 rotatably disposed inside of the outer ring. The inner surface 102 of the outer ring and the exterior surface 103 of the adjustment ring have a plurality of teeth, tabs, or other suitable locking type devices to prevent the adjustment member from rotating in two directions.

Referring to FIG. 4, the depicted device includes a plurality of gear/ratchet teeth 113 on the exterior surface of the adjustment ring and a plurality of flexible tabs 118 on the interior surface of the outer ring to work similar to a ratchet and pawl type device. The tabs 118 are formed from a biocompatible material having sufficient elastic properties to allow the tabs to be pressed flat against the interior surface of the outer ring and then spring back into a first position where they are angled away from the outer ring. The tabs can be formed integrally to the outer ring from the same piece of material as the ring member, or they can be formed separately and affixed to the ring member. The teeth 113 have an inclined side that faces the direction of rotation and a flat side at a right angle to the exterior surface of the adjustment ring. The teeth 113 can be formed integrally to the adjustment member from the same material as the ring or they can be formed separately and affixed to the exterior surface of the adjustment ring. In one embodiment, the teeth are cut into the surface of the adjustment ring and the tabs are cut into a thin ring of shape memory material and the ring is attached to the inner surface of the outer ring. In another embodiment of the invention, the tabs are cut from a thin ring of nitinol that is affixed to the inner surface of the outer ring.

The rings are sized such that the adjustment ring fits inside the outer ring with just enough room for the tabs 118 to fit between the tip of the teeth 113 and the inner surface of the outer ring. When the adjustment ring is rotated in the direction of the arrow, the tabs slide along the inclined surface of the teeth on the adjustment member until the tab is pressed flat against the interior surface of the outer ring. When the tips of the teeth reach the ends of the tabs, the tabs recoil into the area between the teeth and butt up against the flat edge of the teeth, thereby preventing the adjustment ring from rotating in the direction opposite the arrow.

An opening 105 communicates through the center of the adjustment ring 104. The adjustment ring is rotated by placing a tool or other instrument in the opening and rotating the tool. The opening in the depicted embodiment is hexagonal, but the opening can have other shapes so long as the tool being used to turn the adjustment ring has a tip with a shape that is complementary to the shape of the opening. The adjustment ring can be made from the same materials as the outer ring, in one embodiment the adjustment ring is made from nitinol, and in another embodiment the adjustment ring is made from a biocompatible polymer.

Referring to FIGS. 2 and 3, an adjustment cord 108 is connected to the proximal end 114 of each outer leg member 112. The adjustment cord can be made from any suitable biocompatible cord-like material, and it can comprise a filament, a string, a wire, or a cable. Examples of suitable cord material include, but are not limited to surgical gut, cotton, silk, polypropylene, polyester, polyamide, polyglycolide, polylactide, and polylactide-glycolide copolymer. In one embodiment of the invention, the cord is a multifilament polypropylene cord.

A first, generally tubular, cord channel 110 communicates through the outer ring 101, and a second, generally tubular, cord channel 111 communicates through a portion of the adjustment ring 104. The adjustment cord 108 extends from the proximal end 114 of the outer leg member 112, through the first 110 and second 111 cord channels, and terminates in a cord stop 109. The cord stop is directly adjacent the distal opening in the second cord channel, and it is larger than the cord channel opening so that it cannot fit through the cord channel. The cord stop can be a knot tied in the end of the adjustment cord, or it can be a bead or other object affixed to the end of the adjustment cord. The adjustment ring 104 includes an outer circumferential groove 106 (outer groove) and an inner circumferential groove (inner groove) 107. The grooves can be cut into the ring or the ring may be cast or formed with the grooves present. The inner groove 107 allows the cord stop to remain out of the center opening 105 of the adjustment ring, and the outer groove 106 allows the cord to be wound around the adjustment ring without binding the two rings and preventing rotation.

After the device has been implanted in the annulus of a heart valve and the tips 117 of the outer leg members 112 are secured, a tool is inserted into the center opening 105 of the adjustment ring 104. The tool is then rotated, which causes the adjustment ring to rotate, and the tabs 118 and teeth 113 work as described above to prevent rotation in both directions. When the adjustment ring is rotated, the cord stop 109 prevents the proximal end of the cord 108 from passing through the second cord channel 111, thereby causing the cord to wind around the adjustment ring. As the cord is wound around the adjustment ring, the distal end of the cord is pulled inward thereby causing the outer leg members to be drawn into the inner leg members 115. When a clinician stops rotating the tool, the outer leg members remain inside of the inner leg members, and the shape of the mitral valve annulus is altered such that the coaption between the leaflets is improved. It will be apparent to one having ordinary skill in the art that the size of the teeth 113 and tabs 118 will affect how fine the adjustment can be made, with a large number of small teeth and tabs allowing for finer adjustments than allowed by a small number of large teeth and tabs.

While it is not depicted in FIGS. 2 and 3, the invention can also comprise a top and bottom cover plate for covering the upper and lower ends of the base. In one embodiment, the cover plates are fastened to the upper and lower surfaces of the outer ring, and they will have an opening that corresponds with the location of the opening in the adjustment ring, so the adjustment ring can be rotated. In another embodiment, the cover plates will be fastened to the adjustment ring and will rotate with the adjustment ring.

Another aspect of the current invention is that the devices described herein have a delivery configuration, a deployment configuration, and a treatment configuration. FIG. 2 is an example of the deployment configuration of a device according to the current invention (where the outer leg members have not been drawn into the inner leg members). The treatment configuration is shown (in FIGS. 13 and 14) and described below (where the device is implanted and the outer leg members are drawn into the inner leg members to alter the shape of the valve annulus).

Figure 8:
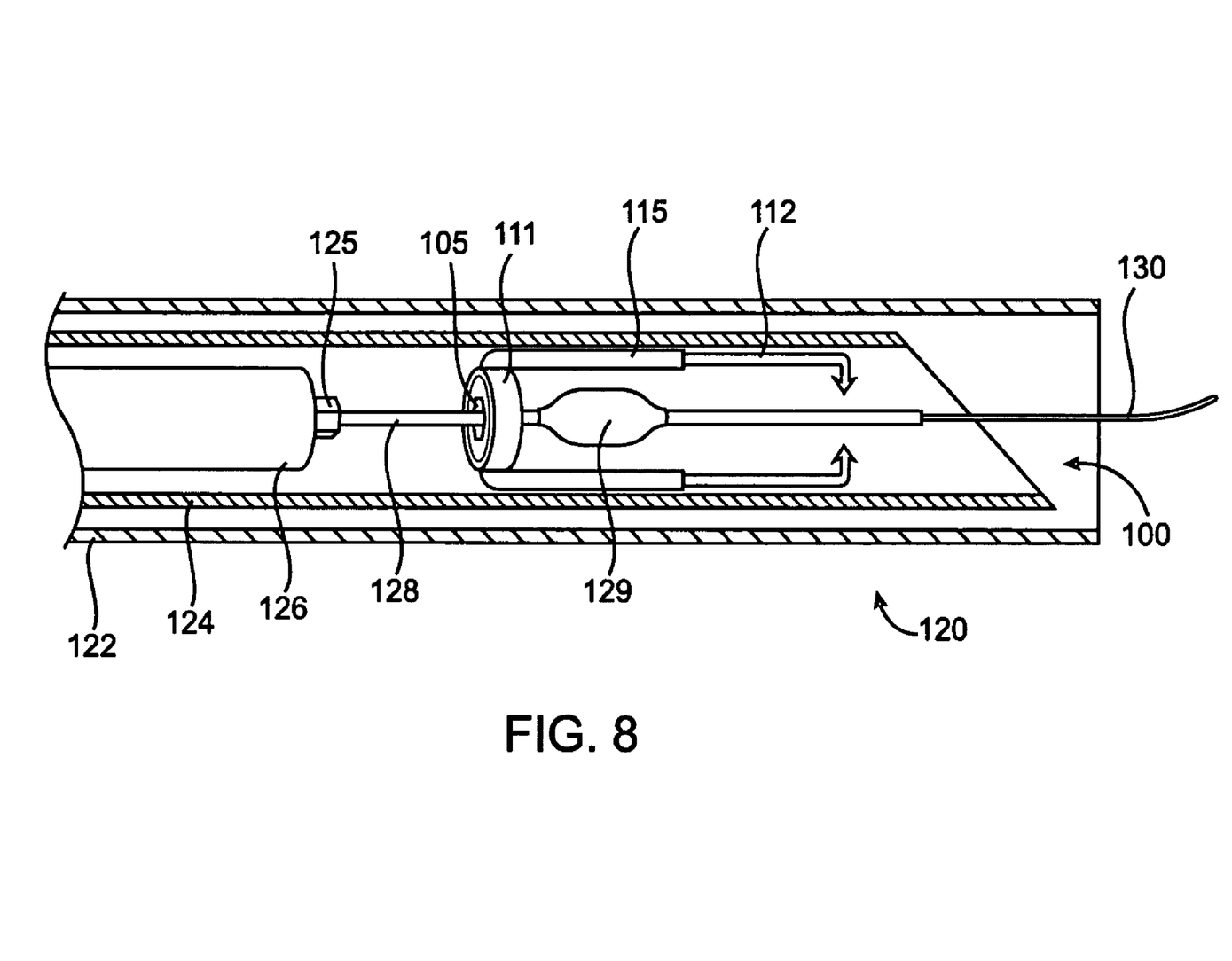
FIG. 8 is a longitudinal cross sectional view of one embodiment of a device according to the current invention, disposed in a delivery catheter.
Figure 10:
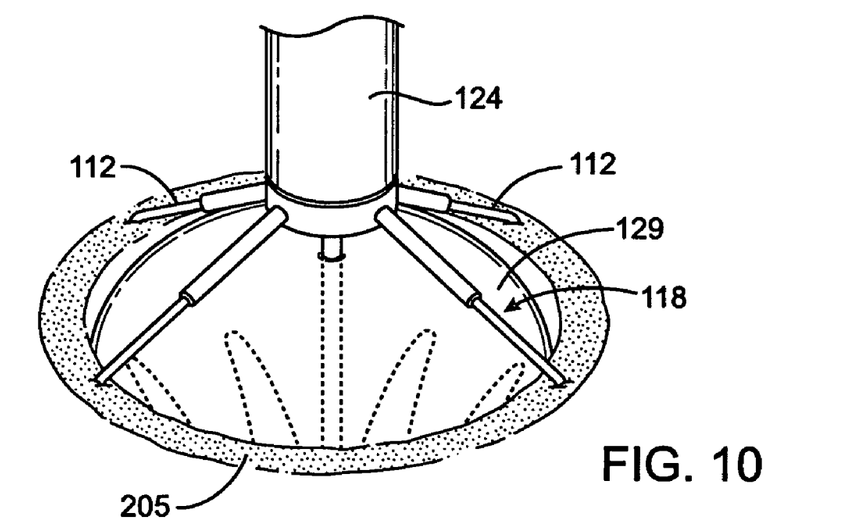

Referring now to FIG. 8, there can be seen a device according to the current invention in a delivery configuration as part of a system that includes a delivery catheter. System 100 includes delivery catheter 120 and guidewire 130. Only a distal portion of the system is illustrated. Besides the two stable deployment and treatment states discussed above, the device may be deformed into a radially compressed configuration when confined within catheter 120 for delivery, as shown in FIG. 8. The device is capable of self-expansion from the radially compressed delivery configuration to the first stable deployment configuration, as shown in FIG. 10.

The compression of device into the radially compressed configuration may be achieved elastically, that is, without any permanent deformation of the device by first making and setting the device in the deployment configuration and then forming it into the delivery configuration shown in FIG. 8. Heat setting the formed device can provide shape memory to the material so that device will return to the deployment configuration from the deformed delivery configuration when the device is delivered to a location adjacent a cardiac valve. When the device is deployed, the shape memory properties of the material from which the device is constructed, cause it to assume the deployment configuration. Those familiar with shape memory materials will readily understand that the device can be formed into the delivery configuration through changes in temperature or through the use of stress.

In the depicted embodiment, delivery catheter 120 comprises guiding sheath 122, holding tube 124, push tube 126, and balloon catheter 128. Holding tube 124 is slidable within a lumen of guiding sheath 122, push tube 126 is slidable within a lumen of holding tube 124, and balloon catheter 128 is slidable within a lumen of push tube 126. At least a portion of balloon catheter 128 is additionally slidable within the opening 105 in the base of the device. Thus, delivery catheter 120 comprises four separate telescoping members, each slidable to be individually extended or retracted as needed to deliver device 110.

Figure 9:
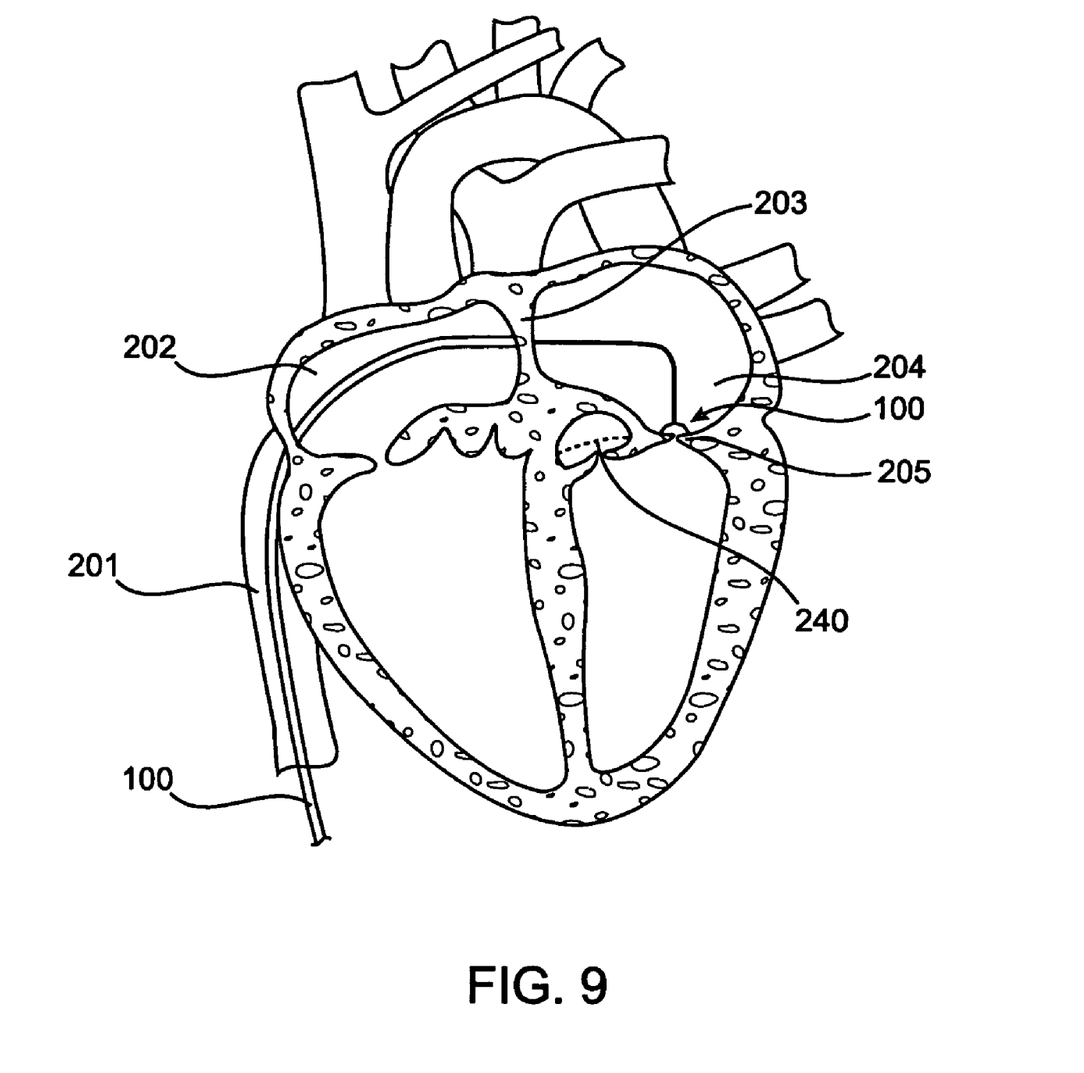
FIGS. 9-12 are views showing a progression of placement of a annulus reshaping device proximate a mitral valve, in accordance with the present invention.

Guiding sheath 122 comprises a flexible, biocompatible material such as polyurethane, polyethylene, nylon, or polytetrafluoroethylene (PTFE). Guiding sheath 122 has a pre-formed or steerable distal tip that is capable of assuming a desired bend with respect to the longitudinal axis of the sheath to aid in delivering the system. In one embodiment, this bend allows system 100 to approach the interatrial septum at the correct orientation to deliver device through the septum as seen in FIG. 9. In the illustrated embodiment, system 100 is passed through inferior vena cava 201 into right atrium 202, then guiding sheath 122 remains within the right atrium while the holding tube and its contents pierce through interatrial septum 203 (also referred to as the septal wall) into left atrium 204 to be positioned adjacent to mitral valve 205. Those skilled in the art will appreciate that alternative paths are available to gain access to the mitral valve.

Holding tube 124 comprises the same or a different biocompatible material from that used to form guiding sheath 122. Like guiding sheath 122, holding tube 124 has a preformed or steerable distal tip that is capable of assuming a desired bend with respect to the longitudinal axis of the tube when the tube is extended beyond guiding sheath 122. Where the tip is pre-formed, the biocompatible material comprising holding tube 124 must allow the distal tip to assume a linear configuration while contained within the guiding sheath and the tip will assume the desired, preformed bend when extended beyond the distal end of guiding sheath 122. In the embodiment shown in FIG. 9, the bend allows system 100 to be directed toward mitral valve 205.

In the depicted embodiment, the distal end of holding tube 124 is angle-cut to form a sharp edge able to pierce through interatrial septum 203. Thus, where device is to be delivered transluminally, holding tube 124 must be flexible enough to be delivered through vasculature to the treatment area while still rigid enough to pierce the septal wall.

Push tube 126 also comprises a biocompatible material. Push tube 126 must be axially flexible for transluminal delivery while being longitudinally incompressible to exert an axial force on body 111 of device 110, as described below. Push tube 126 further includes an adjustment member 125 located on its distal end. The adjustment member has a complementary shape to the opening 102 in the adjustment ring so that the adjustment member can be inserted into the opening, and rotated by rotating the push tube 126.

In the depicted embodiment, balloon catheter 128 includes a single low-pressure balloon 129. During delivery, balloon 129 is positioned between legs 118 of device as shown in FIG. 8. The balloon may be partially inflated to a diameter greater than the diameter of the opening 105 in the base of device 110, thereby serving to secure the device in the catheter system during delivery.

For delivery, system 100 is in the configuration shown in FIG. 8, with device slidably received within delivery catheter 120. Delivery catheter 120 is passed through the venous system and into a patient's right atrium adjacent to the mitral valve. This may be accomplished as shown in FIG. 9, in which delivery catheter 120 has been inserted through the femoral vein into the common iliac vein, through inferior vena cava 201 into right atrium 202, and then at least a portion of the delivery catheter is passed through septal wall 203 into left atrium 204 and positioned adjacent to mitral valve 205.

Other paths are available, including through the radial vein into the brachial vein, through the subclavian vein, through the superior vena cava into the right atrium, and then transeptally into the left atrium. Yet another possible path would be through the femoral artery into the aorta, through the aortic valve into the left ventricle, and then through the mitral valve into the left atrium. Still another possible path would be through the left or right pulmonary vein directly into the left atrium. For surgical approaches with an open chest, the delivery catheter may be replaced by an elongate element such as an endoscope, or a trocar or cannula inserted directly into the superior vena cava or the aortic arch. The elongate element can then follow the same path as the catheter-based procedure to reach the left atrium, either transeptally or through the cardiac valves. Transeptal approaches, whether percutaneous or surgical, may require placement of a closure device at the transeptal puncture on removal of the catheter or other elongate element after the procedure.

In FIG. 10, device is shown released from delivery catheter 120 with legs 118 self-expanded, the device having assumed its stable deployed state. In the depicted embodiment, push tube 126 propels device out of holding tube 124, at which time legs 118 self-expand or splay away from the longitudinal axis of base 119. Alternatively, device may be released by retracting holding tube 124 while maintaining device stationary with push tube 126. Guiding sheath 122 remains in right atrium 202, supporting the delivery system while holding tube 124 and its contents are advanced through septal wall 203 and into position adjacent to mitral valve 205.

Balloon catheter 128 and push tube 126 may be extended from holding tube 124 simultaneously to maintain balloon 129 in a position distal to body 111 and substantially within legs 118. In the depicted embodiment, balloon catheter 128 is directed over guidewire 130, which is passed through mitral valve 205 prior to extending balloon catheter 128. Balloon 129 is expanded at approximately the same time device is released from holding tube 124. As seen in FIG. 10, balloon 129 is positioned over and partially within mitral valve 205. Balloon 129 thus acts as both a retaining device and a positioning device to ensure proper placement of device over the valve annulus.

Figure 11:
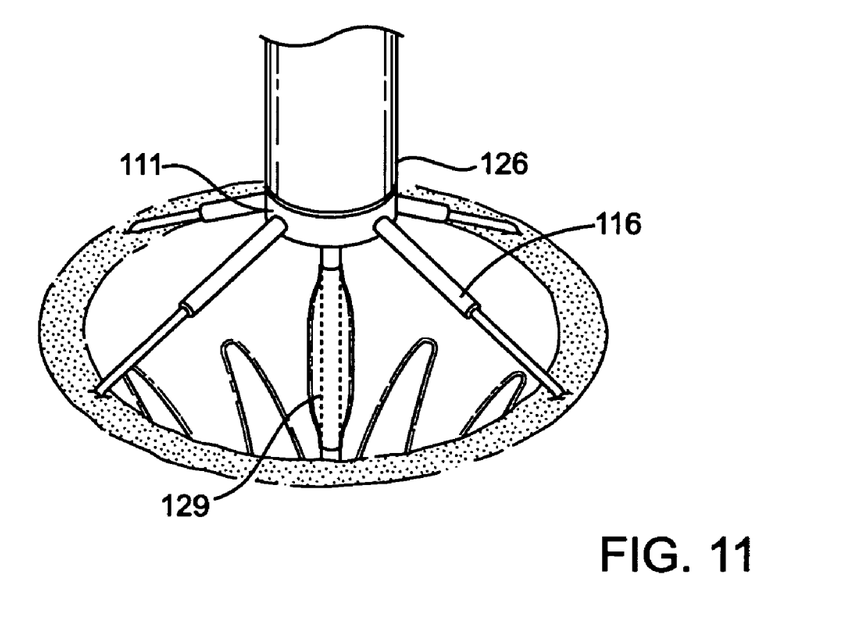

As shown in FIG. 11, balloon 129 is then at least partially deflated. At the same time, push tube 126 exerts an axial force on body 111 to drive device into contact with the mitral valve annulus (205 in FIG. 10). As push tube 126, now acting as a compression device, continues to exert an axial force on the base of the device and the tips on the ends of outer leg members are driven into the annulus and retained by the barbs on the tips.

Figure 12:
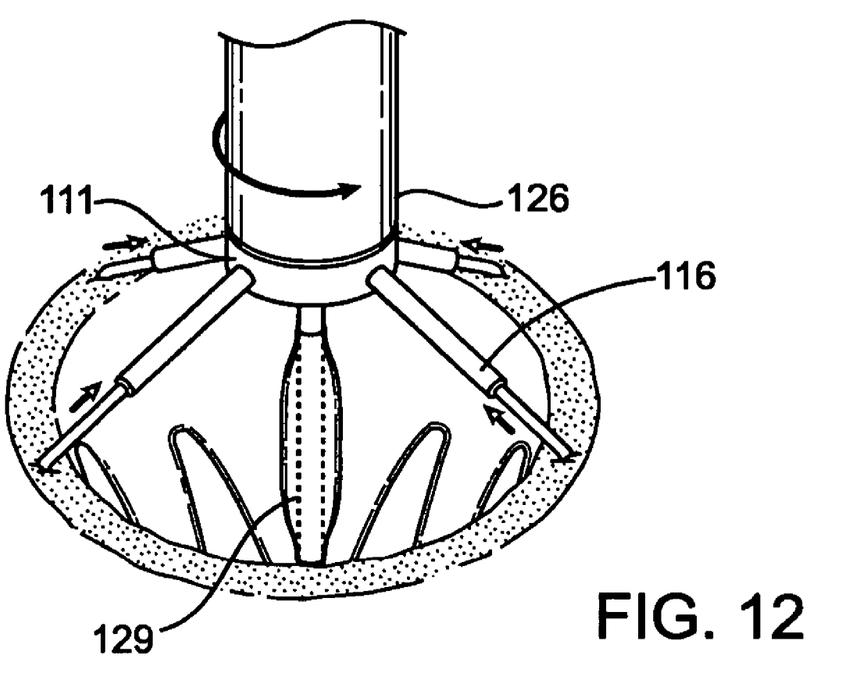

Referring now to FIG. 12, the push rod is now rotated to rotate the adjustment ring and draw the adjustment cord into the first circumferential groove, thereby causing the outer leg members to be drawn into the inner leg members as described above. This action causes the legs to be shortened and the device is thus transitioned into a treatment state. Once the device has assumed its treatment state, thereby altering the shape of the valve annulus and affecting a mitral valve repair, balloon 129 may be deflated and withdrawn through opening 105, allowing delivery catheter 120 to be removed from the body.

Another embodiment of the current invention (not shown) does not include a balloon as part of the delivery system. Instead, the adjustment member on the end of the push tube fits snugly into the opening in the adjustment ring of the device such that the device will remain on the distal tip of the push tube until after the tips of the legs have been implanted. After the device is delivered from the distal end of the delivery catheter and the legs extend to the deployment configuration, the push tube is used to position the device. Once the tips have been implanted in the annulus, the device is transitioned into the treatment configuration as described above.

Figure 13:
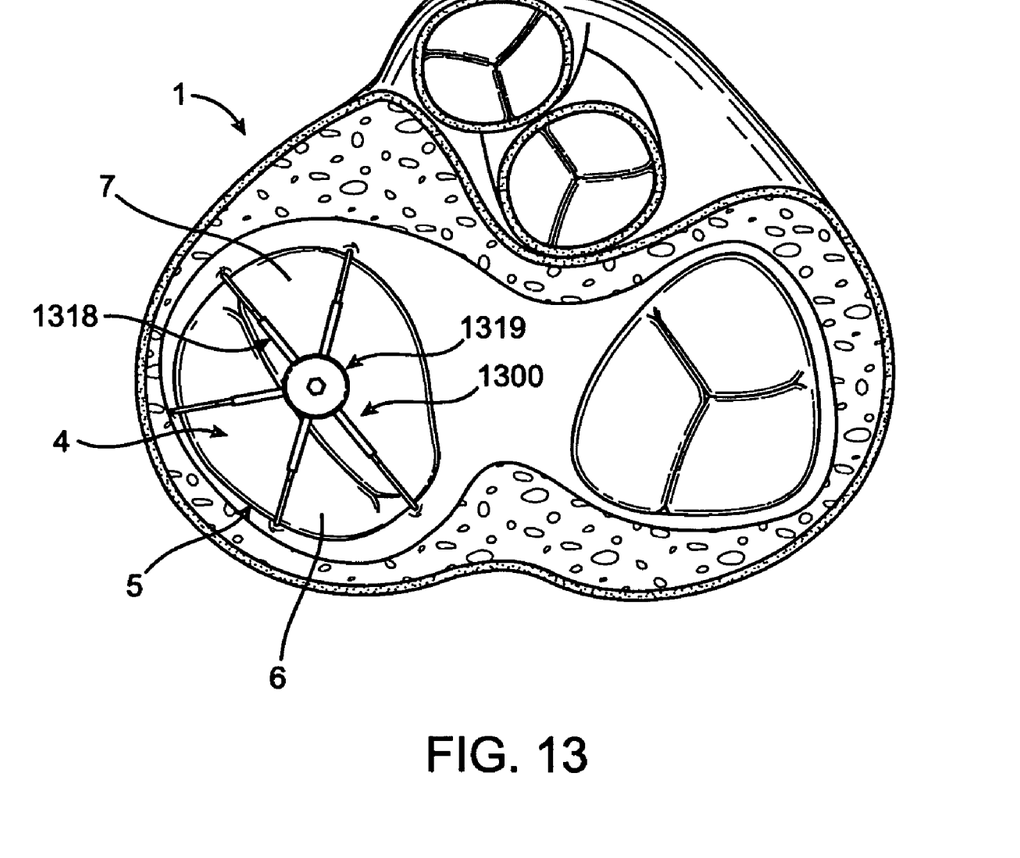
FIGS. 13 and 14 are illustrations depicting the placement of embodiments of the current invention for treating mitral regurgitation.
Figure 14:
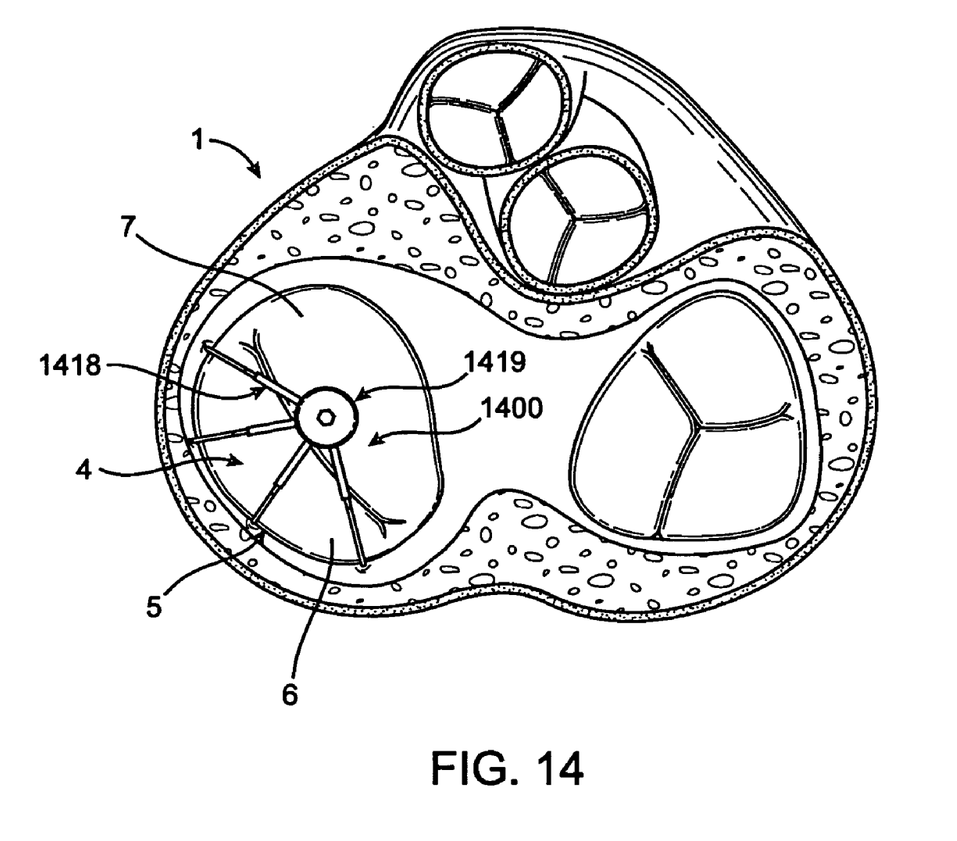

Referring to FIGS. 13 and 14, there can be seen devices according to the current invention in treatment configurations for altering the shape of a mitral valve annulus. The device depicted in FIG. 13 is similar to the device having five legs depicted in FIG. 2 and includes a top cover over the outer ring and adjustment ring as described above. The tips of the legs 1318 are implanted into the annulus 5 of the mitral valve 4, with legs on both the posterior leaflet 6 and the anterior leaflet 7 sides of the valve. In the treatment configuration, the device alters the shape of the annulus and draws the leaflets closer together to improve coaption and reduce regurgitation.

FIG. 14 depicts an embodiment of the current invention having four legs. In this embodiment, the tips of all four legs are inserted into the annulus 5 of a mitral valve 4 on the posterior leaflet 6 side of the valve. When the legs are shortened, the shape of the annulus is altered and coaption of the leaflets is improved. While the devices in FIGS. 13 and 14 have been depicted as having five and four legs respectively, the number of legs for devices being anchored on both the anterior and posterior sides of the valve can be more than and less than five, and the number of legs for devices anchored only on the posterior side of the valve can be more than and less than four.

One skilled in the art will appreciate that numerous other embodiments of the system are possible and that such embodiments are contemplated and fall within the scope of the presently claimed invention. For example, the system described above may further include a gripping device, for example biopsy forceps, for holding the device until it is properly positioned upon the valve annulus. In yet another alternative, the balloon catheter may include two balloons, one initially positioned proximal to the opening 105 and the other positioned distal to the aperture. The distal balloon is a low pressure balloon as described above, and the proximal balloon is a high pressure balloon capable both of pushing the device out of the delivery catheter and of exerting an axial force on the device.

In one embodiment of the current invention, the devices are made of a biocompatible material having a two way shape memory. In this embodiment, the device is first formed and set in a treatment configuration. The legs are then stretched to the length of the deployment configuration and the device is then formed into the delivery configuration. When the device is expelled from a delivery catheter/sheath it will self expand to the deployment configuration and the tips of the legs are inserted into the mitral valve annulus. Energy is then applied to the device, and the legs contract to the treatment configuration thereby altering the shape of the annulus and reducing regurgitation.

Still another alternative includes a magnetic guidewire positioned within the coronary sinus prior to deployment of the device in the atrium. For example, guidewire 240, shown in phantom in FIG. 9 may be magnetic. In this embodiment, the legs of the device are magnetic. Upon deployment of the device within the atrium, the magnetic guidewire acts as a positioning device to attract the device, causing the device to be properly drawn into position.

Figure 15:
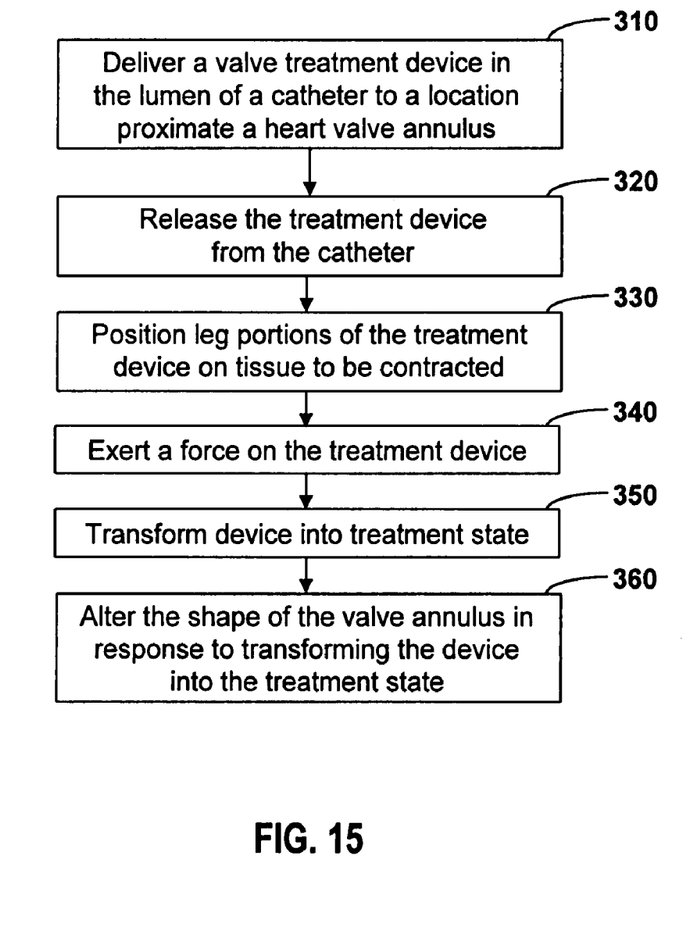
FIG. 15 is a flow diagram of one embodiment of a method of altering the shape of a heart valve annulus, in accordance with the present invention.

Another aspect of the present invention is a method of altering the shape of a cardiac valve annulus. FIG. 15 shows a flow diagram of one embodiment of the method in accordance with the present invention.

A device is delivered in a lumen of a catheter, to a location proximate a treatment area (Block 310). In the depicted embodiment, the device and catheter are those comprising system 100, as described above.

The device is released from the catheter (Block 320). In the depicted embodiment, this is accomplished by extending push tube 126 to propel device out of holding catheter 124.

Legs of the device are positioned on the valve annulus (Block 330). In the depicted embodiment, the legs are positioned on a mitral valve annulus. As described in detail above and shown in FIG. 10, balloon 129 of balloon catheter 128 is positioned partially within mitral valve 205, thereby positioning legs 118 of device on the valve annulus.

A force is exerted on the device (Block 340). In the depicted embodiment, this is accomplished by push tube 126 exerting an axial force on body 111 of device 110. The tips of legs 118 are embedded within the tissue of the valve annulus, and device is transformed into a treatment state (Block 350) by rotating the push tube as described above. The shape of the valve annulus is altered in response to the device attaining its contracted, treatment state (Block 360). Those of skill in the art will recognize that the phrase "diameter of the valve annulus" is used for simplicity in teaching the invention; a mitral valve is not exactly circular, being more D-shaped. Thus, it will be understood that, in the treatment state, each leg 118 of device may shorten a corresponding radial dimension of tissue engaged by the device.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A device for altering the shape of a heart valve annulus, comprising:
    a base having an exterior perimeter;
    a plurality of legs radially arranged about the exterior perimeter and extending from to the base;
    each leg having a proximal end fixed to the base and a distal end;
    each leg including a tip engageable with a valve annulus;
    each leg having an inner section and an outer section, the inner section being fixed to the base at a proximal end of the section, the outer section having the tip located on a distal end thereof, and the inner section and the outer section being slidably connected such that the outer section can telescopically slide along a portion of the inner section;
    each leg further having a first length and a second length and each being capable of transformation between the first length and the second length;
    a plurality of adjustment cords each having a first end attached to the outer section of one of the plurality of legs; and
    an adjustment member that is rotatably connected to the base and a second end of each adjustment cord is attached to the adjustment member such that when the adjustment member is rotated, the adjustment cords are wrapped around the adjustment member and the tip of the outer section of the legs are drawn toward the base.

2. The device of claim 1 wherein the adjustment member has a ratchet and pawl configuration so that it can only rotate in one direction.

3. The device of claim 1 wherein at least the legs comprise a material selected from a group consisting of a nickel-titanium alloy, a nickel-cobalt alloy, a cobalt alloy, a thermoset plastic, stainless steel, a stainless steel alloy, a biocompatible shape-memory material, a biocompatible material having superelastic properties, a biocompatible material having thermoelastic properties, and a combination thereof.

4. The device of 1 wherein the device has a delivery configuration for delivery to location adjacent to a heart valve via a catheter, a deployment configuration, and a treatment configuration.

5. The device of claim 1 wherein the legs are made from a material having shape memory properties and the means for causing the legs to transform from the first length to the second length is a change in temperature.

6. The device of claim 1 wherein the first length of the legs is longer than the second length.

7. The device of 1 wherein the plurality of legs is at least four legs.

8. The device of claim 1 wherein at least a portion of the device includes a therapeutic agent selected from a group consisting of an antithrombotic, an anticoagulant, an antibiotic, an anti-inflammatory, and a combination thereof.

9. The device of 1 wherein at least a portion of the device is radiopaque.

* * * * *